United States Patent [19]

Lynch et al.

[11] 4,092,847
[45] June 6, 1978

[54] FLASH POINT ANALYZING MEANS AND METHOD

[75] Inventors: Charles R. Lynch, Port Neches; Robert A. Wheeler, Beaumont, both of Tex.

[73] Assignee: Texaco Inc., New York, N.Y.

[21] Appl. No.: 809,513

[22] Filed: Jun. 23, 1977

[51] Int. Cl.$^2$ ............................................. G01N 25/52
[52] U.S. Cl. ........................................ 73/36; 364/502; 364/557
[58] Field of Search ............. 73/36; 235/151.12, 151.3

[56] References Cited

U.S. PATENT DOCUMENTS

| | | | |
|---|---|---|---|
| 2,119,786 | 6/1938 | Kallam | 73/36 |
| 2,126,052 | 8/1938 | Smith | 73/36 |
| 3,748,894 | 7/1973 | White et al. | 73/36 |

*Primary Examiner*—James J. Gill
*Attorney, Agent, or Firm*—Thomas H. Whaley; Carl G. Ries; Ronald G. Gillespie

[57] ABSTRACT

An analyzer for analyzing the flash point of a product in a process comprising a steam stripper receiving a stream of material and receiving steam includes sensors sensing the temperatures of the material, the steam and the product which provide corresponding signals. Other sensors sense the flow rates of the material, the steam, and the product and provide corresponding signals. The pressure in the top of the stripper is also sensed and a corresponding signal provided. Apparatus samples the product and provides signals corresponding to at least two predetermined parameters of the product. A circuit receiving the signals from the sensors, and from the apparatus provide a signal corresponding to the flash point temperature of the product in accordance with the signals from the sensors and the apparatus.

24 Claims, 13 Drawing Figures

FLASH POINT MEANS 35

FLASH POINT ANALYZING MEANS AND METHOD

BACKGROUND OF THE INVENTION

1. Field of the Invention

The present invention relates to analyzers and analyzing methods, in particular.

2. Description of the Prior Art

U.S. Pat. No. 3,748,894, which issued July 31, 1973 and is assigned to Texaco Inc., assignee of the present invention, concerns itself with flash point analyzers for lube oil fractions. The present invention differs from the aforementioned patent in that it is not restricted to lube oil fractions but can be utilized for a greater range of stocks. Further, it senses more parameters than the invention of the aforementioned U.S. patent, so that it can provide a more accurate determination of the product's flash point temperature.

SUMMARY OF THE INVENTION

A flash point analyzer for use with a steam stripper, receiving a stream of material and steam and providing a product, includes sensors sensing the temperatures of the material, the steam and the product and providing signals corresponding thereto. Other sensors sense the flow rates of the steam and the product and provide corresponding signals. A pressure in the stripper is also sensed by a sensor which provides a corresponding signal. Apparatus samples the product and provides signals corresponding to at least two predetermined parameters of the product. A circuit connected to all the sensors and the sampling apparatus provides a signal corresponding to the product's flash point temperature in accordance with the temperature signals, the flow rate signals and the parameter signals from the apparatus.

The objects and advantages of the invention will appear more fully hereinafter from a consideration of the detailed description which follows, taken together with the following drawings wherein two embodiments of the invention are illustrated by way of example. It is to be expressly understood, however, that the drawings are for illustration purposes only and are not to be construed as defining the limits of the invention.

DESCRIPTION OF THE INVENTION

Figure 1:
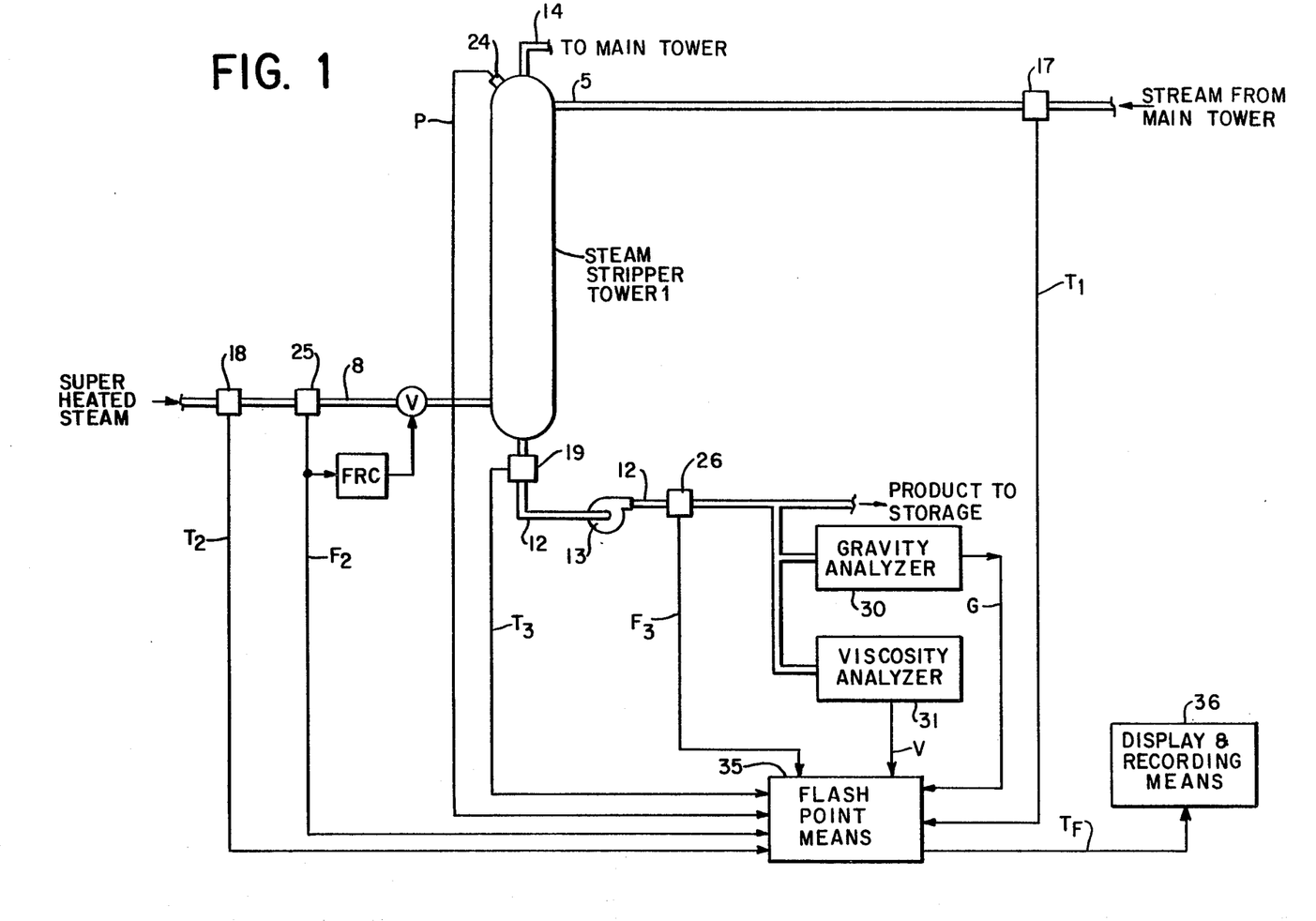
FIG. 1 is a simplified block diagram of apparatus, constructed in accordance with the present invention, for providing a signal corresponding to the flash point temperature of a product from a steam stripper being monitored by the apparatus in a refinery.

Referring to FIG. 1, there is shown a steam stripper tower 1, having N number of trays (not shown) and receiving a stream from a main tower (not shown) by way of a line 5. Superheated steam is provided to tower 1 by way of a line 8 where tower 1 strips a hydrocarbon product from the stream and provides the product by way of a line 12 which is pumped by a pump 13 to storage. A line 14 vents tower 1 to the main tower. Conventional type temperature sensors 17, 18 and 19 sense the temperatures of the stream in line 5, the superheated steam in line 8 and the product in line 12, respectively, and provide corresponding temperature signals $T_1$, $T_2$ and $T_3$, respectively. The flow rate of the superheated steam in line 8 and the product in line 12 are sensed by flow rate sensors 25 and 26, respectively, which provide flow rate signals $F_2$ and $F_3$, respectively. The pressure in the top of tower 1 is sensed by pressure sensor 24 to provide pressure signal P. It would be obvious to one skilled in the art to sense a pressure anywhere in tower 1 and relate it to the pressure at the bottom tray. The product in line 12 is sampled by a gravity analyzer 30 and a viscosity analyzer 31 which provide signals G and V, respectively, corresponding to the API gravity and to the viscosity of the product, respectively.

All signals are provided to flash point means 35 which provides a signal $T_F$ corresponding to the flash point temperature of the product to display and recording means 36. Display and recording means 36 may contain conventional type display means and recording means for displaying and recording signal $T_F$.

The following equations are used in the flash point determination of a high boiling stock such as lube oil.

$$T_4 = T_3 + (T_1 - T_3)/N \tag{1}$$

where $N$ is the number of trays in tower 1 and $T_1$, $T_3$ and $T_4$ are the temperatures in degrees Fahrenheit of the stream in line 5 and the product in line 12 and the temperatures of the liquid in degrees Fahrenheit flowing to the bottom tray.

$$K = C_1 + C_2 G - C_3/V \tag{2}$$

where $C_1$ through $C_3$ are constants having preferred values of 10.04, 0.0794 and 36.8, respectively; $G$ is the API gravity of the product and $V$ is the viscosity, SUS at 100° F, of the product; and $K$ is the Watson $K$ factor.

$$H_{L4} = C_4(C_5K+C_6)[(C_7+C_8G)T_4+C_9(C_{10}+C_{11}G)T_4^2] \tag{3}$$

where $C_4$ through $C_{11}$ are constants having preferred values of 0.01, 0.055, 0.35, 38, 0.12, 0.0001, 257 and 0.6, respectively; and $H_{L4}$ is the enthalpy of the liquid in BTU per pound flowing to the bottom tray.

$$H_{L3} = C_4(C_5K+C_6)[(C_7+C_8G)T_3+C_9(C_{10}+C_{11}G)T_3^2] \tag{4}$$

where $H_{L3}$ is the enthalpy of the liquid (product) in BTU per pound flowing to the bottom tray.

$$H_{V3} = C_{12}T_3^2+C_{13}T_3+C_{14}+C_{15}G+C_{16}(K-C_{17})(T_3-C_{18}) \tag{5}$$

where $C_{12}$ through $C_{18}$ are constants having preferred values of 0.000255, 0.32, 126, 0.8, 0.06, 11.8 and 400, respectively; and $H_{V3}$ is the enthalpy of the vapor in BTU per pound from the bottom tray.

$$F_5 = [F_3[C_{19}/(C_{20}+G)](H_{L4}-H_{L3})+C_{21}(T_2-T_3)F_2]/(H_{V3}-H_{L4}) \quad (6)$$

where $C_{19}$, $C_{20}$ and $C_{21}$ are constants having preferred values of 49525, 131.5 and 0.5, respectively; $F_2$, $F_3$ and $F_5$ are the flow rates of the steam in line 8 in pounds per hour, of the product in line 12 in barrels per hour and of the vapor stripped from the bottom tray in pounds per hour; and $T_2$ is the temperature of the steam in line 8 in degrees Fahrenheit.

$$M = C_{22}[G-C_{23}(K-C_{24})]^2 - C_{25}[G-C_{23}(K-C_{24})]+C_{26} \quad (7)$$

where $C_{22}$ through $C_{26}$ are constants having preferred values of 0.185, 17.5, 11.5, 21.27 and 709.4, respectively; and $M$ is the molecular weight of the product.

$$P_3 = [C_{27}(P+\Delta P)(F_5/M)]/C_{28}(F_5/M-F_2/C_{29}) \quad (8)$$

where $C_{27}$, $C_{28}$ and $C_{29}$ are constants having preferred values of 14.69, 760 and 18, respectively; $P$ is the pressure in the top of tower 1 in millimeters of mercury, $P_3$ is the partial pressure of hydrocarbon vapors above the bottom tray in pounds per square inch absolute, and $\Delta P$ is the pressure drop across tower 1 in millimeters of mercury and has an assumed value based on experience.

$$\log P_3 = C_{30}-C_{31}Z_B+C_{32}Z_B^2-C_{33}Z_B^3+C_{34}Z_B^4-C_{35}Z_B^5+C_{36}Z_B^6 \quad (9)$$

where $C_{30}$ through $C_{36}$ are constants having preferred values of 5.32159, 4615.5, 2.617454×10⁶, 1.601348×10⁹, 4.326421×10¹¹, 5.257646×10¹³ and 2.274413×10¹⁵, respectively; and $Z_B$ is an intermediate variable.

$$T_B = (C_{37})(Z_B)/[C_{41}/(T_3+C_{38})-C_{39}+C_{40}Z_B] \quad (10)$$

where $T_B$ is the estimated boiling point of the product in degrees Fahrenheit and $C_{37}$ through $C_{41}$ are constants having preferred values of 748.1, 459.7, 2.867×10⁻⁴ and 0.2145 and 1.0, respectively.

$$\log P_F = C_{30}-C_{31}Z_F+C_{32}Z_F^2-C_{33}Z_F^3+C_{34}Z_F^4-C_{35}Z_F^5+C_{36}Z_F^6 \quad (11)$$

where $P_F$ is the vapor pressure at the flash point in pounds per square inch absolute, which is 0.063 psia for a light lube oil stream, and $Z_F$ is an intermediate variable.

$$T_F = [T_B/[Z_F(C_{37}-C_{40}T_B)+C_{39}T_B]]C_{38} \quad (12)$$

where $T_F$ is the flash point temperature in degrees Fahrenheit.

In another embodiment, the flash point determination for a low boiling stock such as kerosine, equation 2 is replaced by the following equation 2A.

$$K = [(G+C_{42})(D+C_{43})^{1/3}]/C_{44} \quad (2A)$$

where $D$ is the ASTM 50% point of the product, $C_{42}$, $C_{43}$ and $C_{44}$ are constants having preferred values of 131.5, 460 and 141.5, respectively. Further $P_F$ in equation 11 has a preferred value of 0.0212 psia for the kerosine stream. It should be noted that in the second embodiment viscosity analyzer 31 would be replaced by another analyzer providing a signal D corresponding to the ASTM 50% point of the product.

Figure 2:
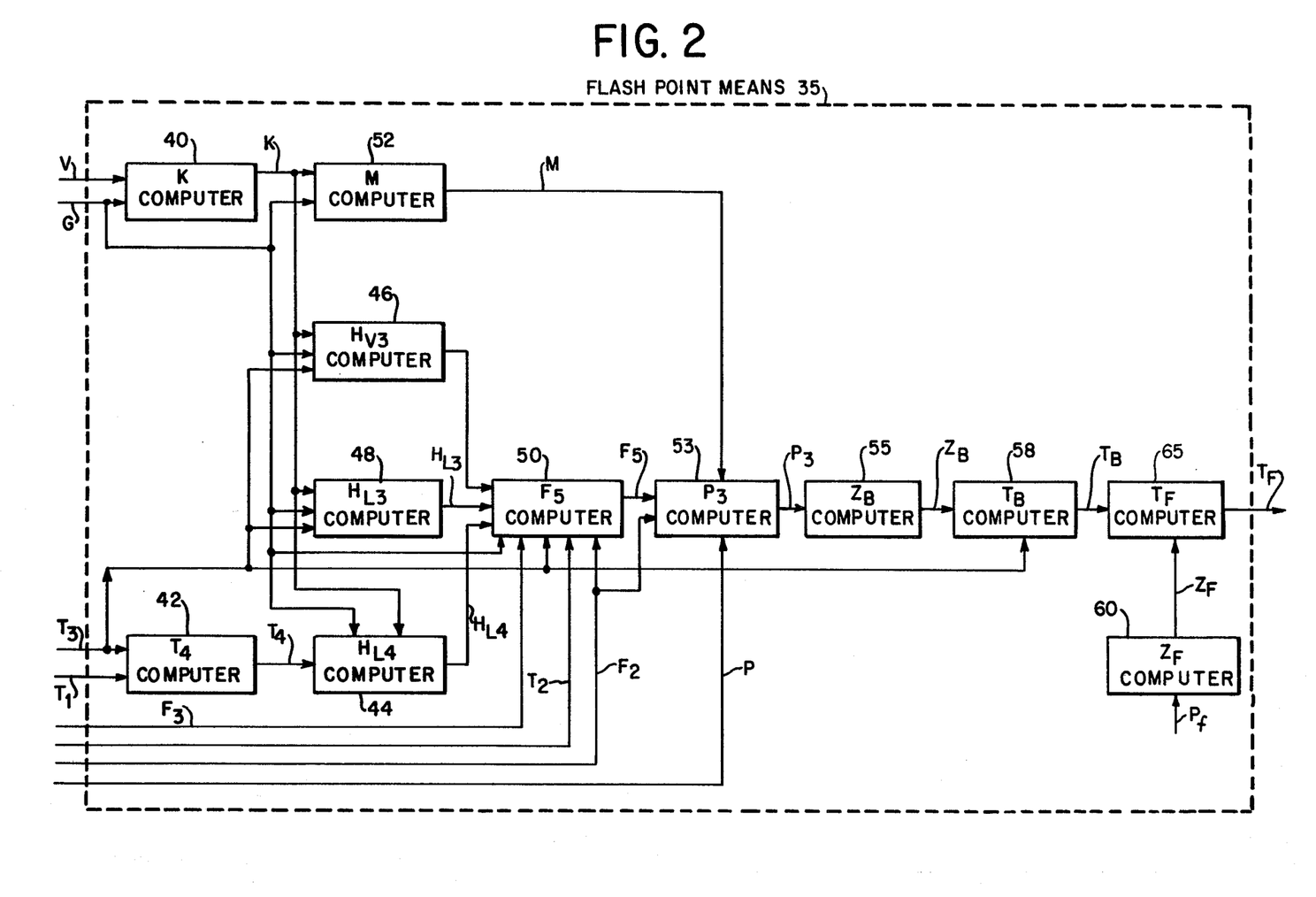
FIG. 2 is a simplified block diagram of the flash point means shown in FIG. 1.

Referring now to FIG. 2, there is shown flash point means 35 wherein a K computer 40 receives signals V and G and provides a signal K in accordance with equation 2. $K_K$ computer 40 will be explained in greater detail hereinafter.

A $T_4$ computer 42 receives temperature signals $T_1$, $T_3$ and provides a temperature signal $T_4$ in accordance with equation 1 as hereinafter explained. A $H_{L4}$ computer 44 receives signals G, K and $T_4$ and provides a signal $H_{L4}$ in accordance with equation 3 as hereinafter explained.

An $H_{V3}$ computer 46 receives signals G, K and $T_3$ and provides signal $H_{V3}$ in accordance with equation 5 as hereinafter disclosed. An $H_{L3}$ computer 48 also receives signals G, K and $T_3$ and provides signal $H_{L3}$ in accordance with equation 4 as hereinafter disclosed.

An $F_5$ computer 50 receives signals $T_2$, $T_3$, $F_2$, $F_3$, G, $H_{V3}$, $H_{L3}$ and $H_{L4}$ and provides a signal $F_5$ in accordance with equation 6 as hereinafter explained.

An M computer 52 receives signals K and G and provides a signal M in accordance with equation 7 as hereinafter explained. A $P_3$ computer 53 receives signals $F_2$, $F_5$, M and P and provides a signal $P_3$ in accordance with equation 8 as hereinafter explained. A $Z_B$ computer 55 receiving signal $P_3$ from computer 53 provides a signal $Z_B$ in accordance with equation 9 as hereinafter explained. A $T_B$ computer 58 provides a signal $T_B$ in accordance with signals $T_3$, $Z_B$ and equation 10 as hereinafter explained. A $Z_F$ computer 60 receiving a direct current voltage $P_F$, corresponding to a predetermined flash point pressure, provides a signal $Z_F$ in accordance with equation 11. A $T_F$ computer 65 receiving signals $T_B$ and $Z_F$ provides the flash point temperature signal $T_F$ in accordance with equation 12.

Figure 3:
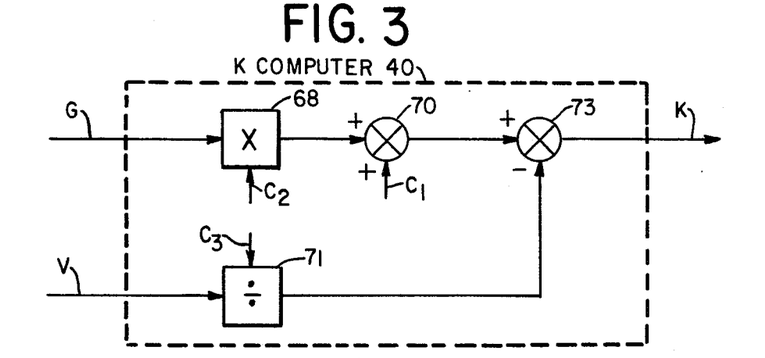
FIGS. 3 through 12 are detailed block diagrams of the K computer, $T_4$ computer, the $H_{L4}$ computer, the $H_{V3}$ computer, the $F_5$ computer, the M computer, the $P_3$ computer, the $Z_B$ computer, the $T_B$ computer and the $T_F$ computer shown in FIG. 2.

Referring now to FIG. 3, there is shown K computer 40 in which signal G is multiplied with a direct current voltage $C_2$ by a multiplier 68 to provide a signal, corresponding to the term $C_2G$ in equation 2, to summing means 70. Summing means 70 sums the signal from multiplier 68 with a direct current voltage $C_1$ to provide a signal corresponding to $C_1+C_2G$ in equation 2. A divider 71 divides a direct current voltage $C_3$ with signal V to provide a signal corresponding to the term $C_3/V$ in equation 2. Subtracting means 73 subtracts the signal provided by divider 71 from the signal provided by summing means 70 to provide signal K.

Figure 4:
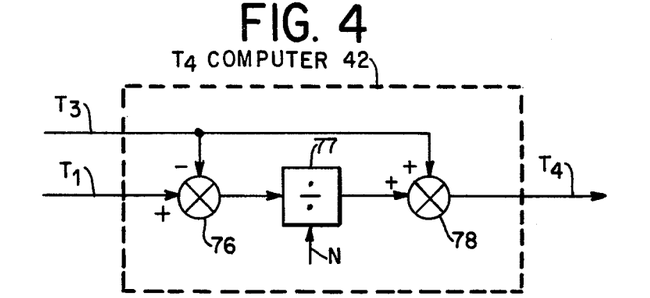

Referring now to FIG. 4, there is shown $T_4$ computer 42 having subtracting means 76 subtracting signal $T_3$ from signal $T_1$ to provide a difference signal to a divider 77. Divider 77 divides the signal from subtracting means 76 with a direct current voltage N to provide a signal corresponding to the term $(T_1-T_3)/N$ in equation 1. Summing means 78 sums signal $T_3$ with the signal from divider 77 to provide temperature signal $T_4$.

Figure 5:
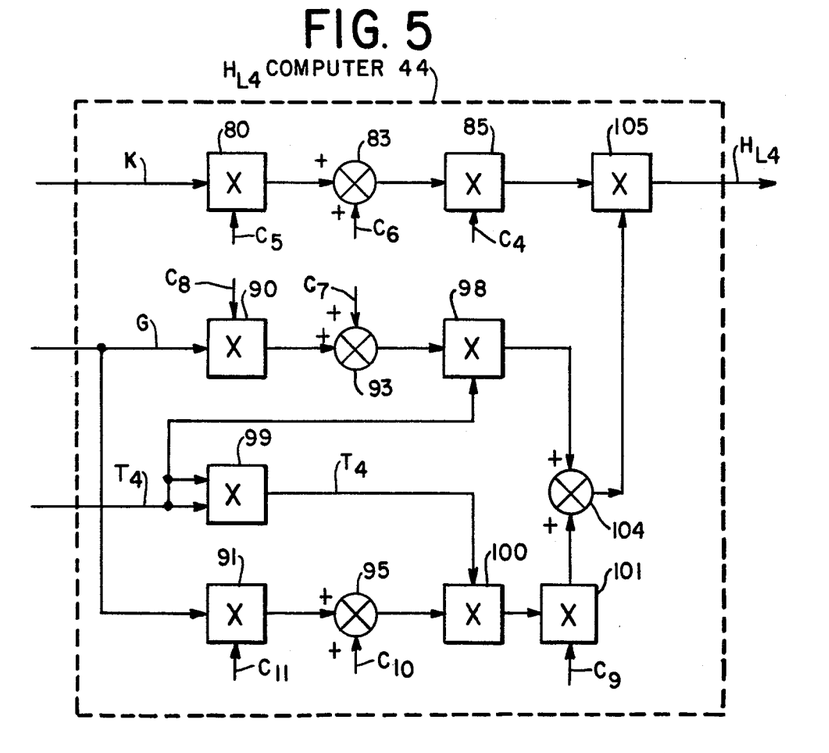

Referring now to FIG. 5, $H_{L4}$ computer 44 includes a multiplier 80 multiplying signal K with a direct current voltage $C_5$ to provide a signal corresponding to the term $C_5K$ in equation 3 and this signal is connected to summing means 83 where it is summed with a direct current voltage $C_6$. A sum signal from summing means 83 is multiplied with another direct current voltage $C_4$ to provide a signal corresponding to the term $C_4(C_5K+C_6)$ in equation 3. Multipliers 90, 91 multiply signal G with direct current voltage $C_8$ and $C_{11}$, respectively, to produce signals to summing means 93 and 95, respectively. Summing means 93, 95 sum the product signals with direct current voltages $C_7$ and $C_{10}$, respectively. The sum signal from summing means 93 is multiplied with signal $T_4$ by a multiplier 98 to provide a signal corresponding to the term $(C_7 + C_8 G)T_4$ in equation 3. Signal $T_4$ is effectively squared by a multiplier 99 whose product signal is multiplied with the sum signal from summing means 95 by a multiplier 100. The product signal from multiplier 100 is multiplied with a direct current voltage $C_9$ by a multiplier 101 which provides a product signal corresponding to the term $C_9(C_{10} + C_{11}G)T_4^2$ in equation 3. Summing means 104 sums the signals from multipliers 98 and 101 to provide a signal to a multiplier 105. Multiplier 105 multiplies the sum signal with the signal from multiplier 85 to provide signal $H_{L4}$.

Figure 6:
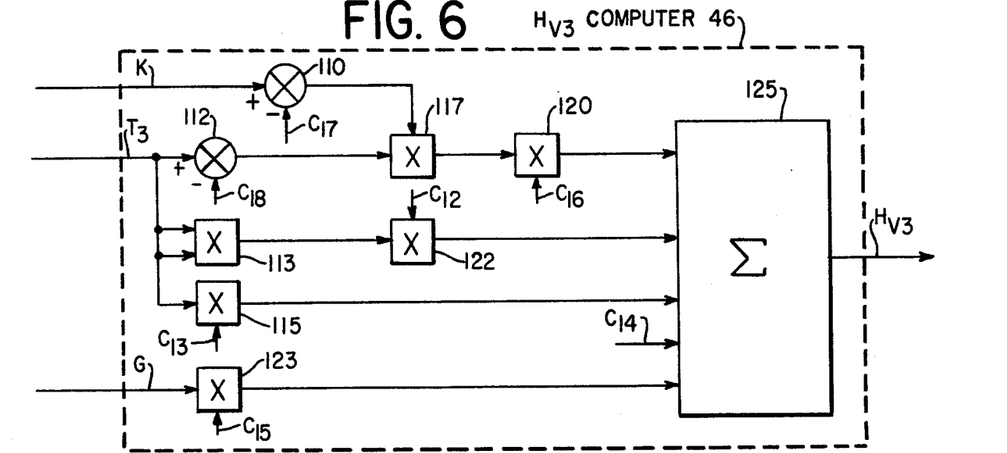

Referring now to FIG. 6 showing $H_{V3}$ computer 46, subtracting means 110, 112 subtract direct current voltages $C_{17}$ and $C_{18}$, respectively, from signals K and $T_3$, respectively, and provide corresponding signals. Signal $T_3$ is also provided to multipliers 113, 115. The signals from subtracting means 110, 112 are multiplied together by a multiplier 117 to provide a signal. Another multiplier 120 multiplies the signal from multiplier 117 with a direct current voltage $C_{16}$ to provide a signal corresponding to the term $C_{16}(K - C_{17})(T_3 - C_{18})$ in equation 5. Multiplier 113 effectively squares signal $T_3$ and provides it to another multiplier 122 where it is multiplied with a direct current voltage $C_{12}$ to provide a signal corresponding to the term $C_{12}T_3^2$ in equation 5. Multiplier 115 multiplies signal $T_3$ with another direct current voltage $C_{13}$ to provide a signal corresponding to the term $C_{13}T_3$ in equation 5. A multiplier 123 multiplies signal G with a direct current voltage $C_{15}$ to provide a signal corresponding to the term $C_{15}G$ in equation 5. Summing means 125 sums the signals from multipliers 120, 122, 115 and 123 with another direct current voltage $C_{14}$ to provide signal $H_{V3}$.

$H_{L3}$ computer 48 is identical in construction to $H_{L4}$ computer 44, the difference in the computers being that signal $T_3$ is used in computer 48 instead of signal $T_4$ which is used in computer 44.

Figure 7:
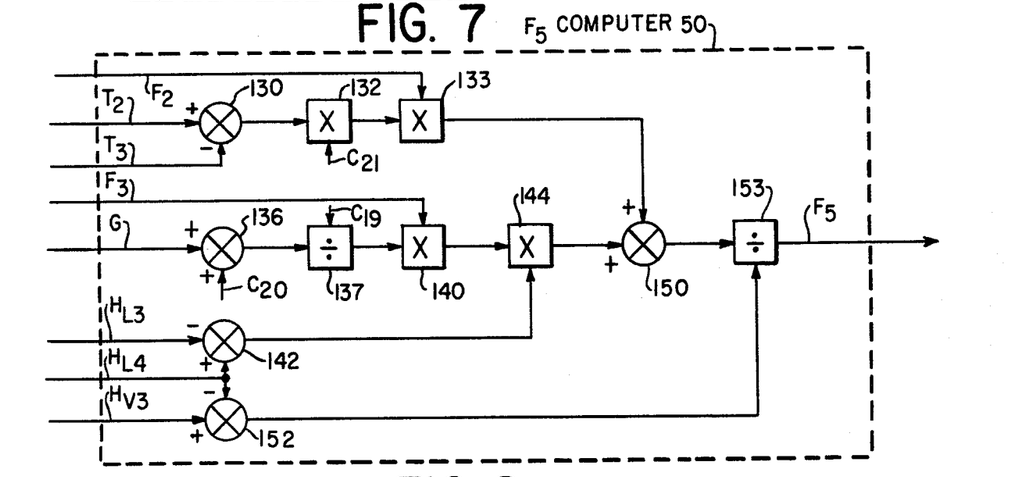

Referring now to FIG. 7 showing $F_5$ computer 50, subtracting means 130 subtracts signal $T_3$ from $T_2$ to provide a difference signal to a multiplier 132. The difference signal is multiplied with a direct current voltage $C_{21}$ by a multiplier 132 to provide a product signal which is multiplied with signal $F_2$ by a multiplier 133. Multiplier 133 provides a signal corresponding to the term $C_{21}(T_2 - T_3)F_2$ in equation 6. Summing means 136 sums signal G with a direct current voltage $C_{20}$ to provide a sum signal which is divided into another direct current voltage $C_{19}$ by a divider 137. Divider 137 provides a signal, corresponding to the term $C_{19}/(C_{20} + G)$, which is multiplied with signal $F_3$ by a multiplier 140 to provide a product signal. Subtracting means 142 subtracts signal $H_{L3}$ from signal $H_{L4}$ to provide a difference signal which is multiplied with the product signal from multiplier 140 by a multiplier 144. Multiplier 144 provides a signal which is summed with the signal provided by multiplier 133 by summing means 150. Subtracting means 152 subtracts signal $H_{L4}$ from signal $H_{V3}$ to provide a difference signal to a divider 153. Divider 153 divides the sum signal from summing means 150 with the difference signal from subtracting means 152 to provide signal $F_5$.

Figure 8:
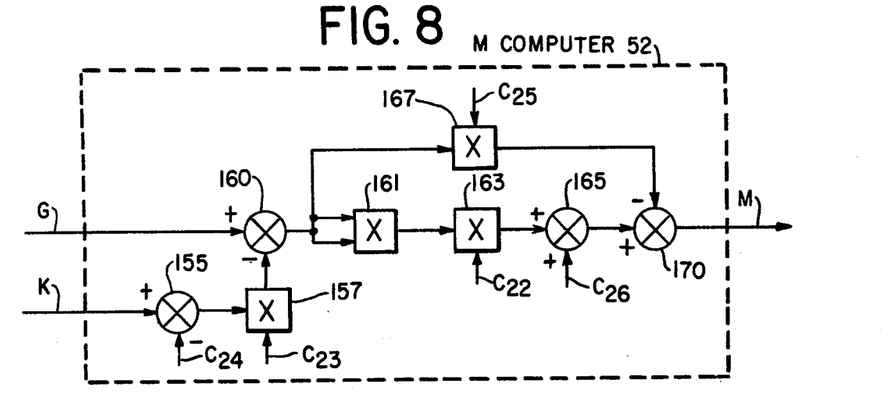

Referring to FIG. 8, there is shown M computer 52 wherein subtracting means 155 subtracts a direct current voltage $C_{24}$ from signal K to provide a difference signal to a multiplier 157. Multiplier 157 multiplies the difference signal with a direct current voltage $C_{23}$ to provide a signal corresponding to the term $C_{23}(K - C_{24})$ in equation 7. Subtracting means 160 subtracts the signal provided by multiplier 157 from signal G to provide a signal corresponding to the term $[G - C_{23}(K - C_{24})]$ in equation 7. The signal from subtracting means 160 is effectively squared by a multiplier 161 and provided to another multiplier 163 where it is multiplied with a direct current voltage $C_{22}$. Summing means 165 sums the signal from multiplier 163 with a direct current voltage $C_{26}$. The signal from subtracting means 160 is also multiplied with a direct current voltage $C_{25}$ by a multiplier 167. Subtracting means 170 subtracts the signal provided by multiplier 167 from the sum signal provided by summing means 165 to provide signal M.

Figure 9:
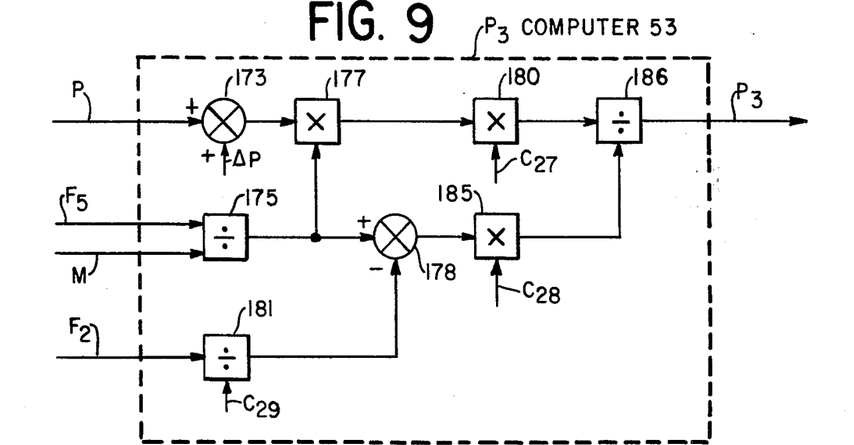

As shown in FIG. 9, signal P is summed with a direct current voltage $\Delta P$, corresponding to a predetermined change in pressure, by summing means 173, in $P_3$ computer 53, to provide a sum signal. A divider 175 divides signal $F_5$ with signal M to provide a signal to a multiplier 177 and to summing means 178. A signal provided by multiplier 177, corresponding to $(P + \Delta P)(F_5/M)$ in equation 8, is multiplied with a direct current voltage $C_{27}$ by a multiplier 180. A divider 181 divides signal $F_2$ with a direct current voltage $C_{29}$ to provide a signal, corresponding to the term $F_2/C_{29}$, to subtracting means 178 where it is subtracted from the signal from the divider means 175 to provide a signal corresponding to the term $(F_5/M - F_2/C_{29})$. The signal from subtracting means 178 is multiplied with a direct current voltage $C_{28}$ by a multiplier 185. A divider 186 divides the signal provided by multiplier 180 with the signal provided by multiplier 185 to provide signal $P_3$.

Figure 10:
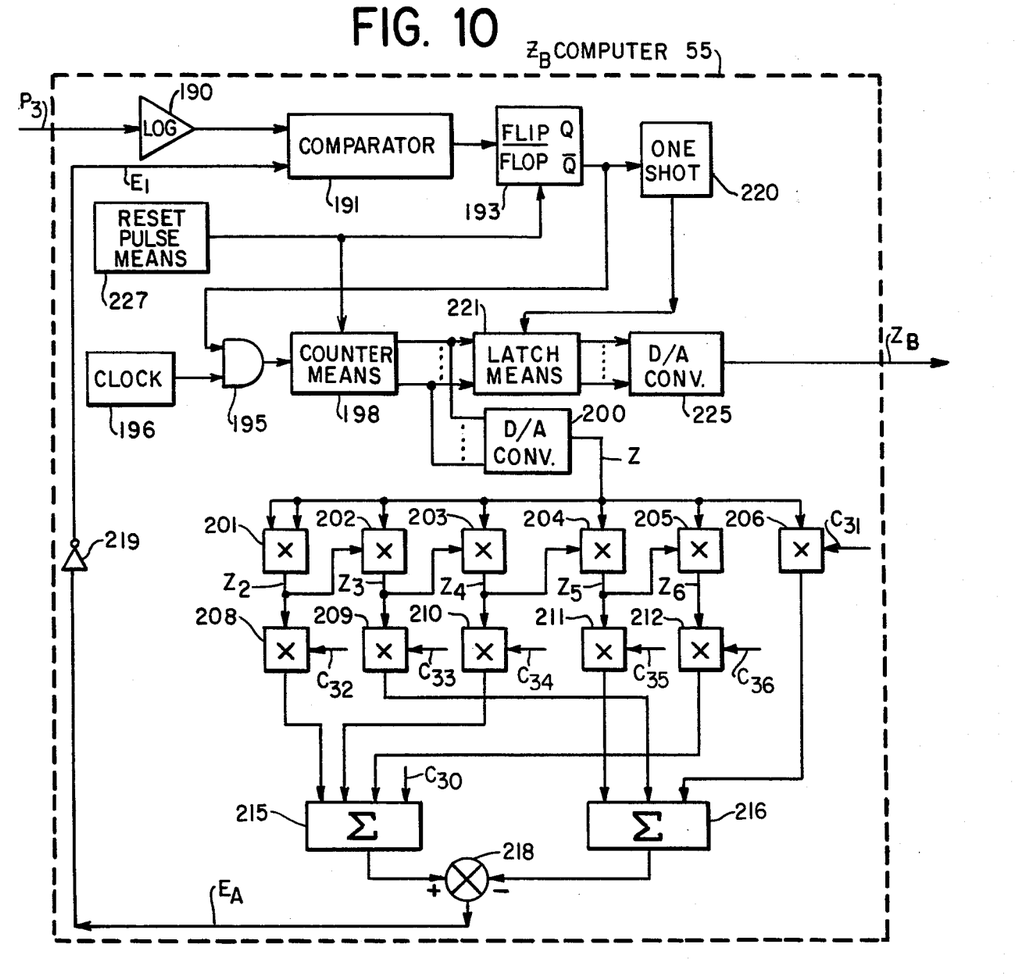

$Z_B$ computer 55, shown in FIG. 10, essentially balances the values of Z in equation 9 with a signal corresponding to log $P_3$. When the proper balance has been achieved, the current value of Z is then provided as signal $Z_B$. With that in mind, signal $P_3$ is provided to a logarithmic amplifier 190 which provides a signal corresponding to log $P_3$ to a comparator 191. Comparator 191 compares the signal from amplifier 190 with a signal $E_1$ corresponding to the right-hand side of equation 9. Comparator 191 provides a signal to a set input of a flip-flop 193. Initially, signal $E_1$ is less than the signal from amplifier 190 causing comparator 191 to provide a high level logic circuit. As soon as signal $E_1$ exceeds the signal from amplifier 190, the signal from comparator 191 changes to a low logic level triggering flip-flop 193 from a 'clear state' to a 'set state'. Flip-flop 193 provides its $\overline{Q}$ output at a high logic level while in a clear state and at a low logic level while in a set state. It should be noted that at this point the current value of Z creates a condition at the right-hand side of equation 9 slightly greater than the signal log $P_3$. However, this slight inaccuracy is immaterial since the right side of equation 9 is substantially equal to log $P_3$. The $\overline{Q}$ output of flip-flop 193 is applied to an AND gate 195 receiving clock pulses from a clock 196. The high logic level of the $\overline{Q}$ output enables AND gate 195 to pass clock pulses to counter means 198. The count in counter means 198 corresponds to the value of Z. It can be seen that as clock 196 provides a pulse, counter means 198 counts it up and provides digital signals corresponding to the count. A digital-to-analog converter 200 converts the digital signals to an analog signal Z. Signal Z from converter 200 is applied to a plurality of multipliers 201 through 206. The outputs of multipliers 201 through 204 are applied to the next highest numbered multiplier of multipliers 202 through 205 so that multipliers 201 through 205 provide signals corresponding to $Z^2$, $Z^3$, $Z^4$, $Z^5$ and $Z^6$, respectively. Multiplier 206 multiplies signal Z with a direct current voltage $C_{31}$ while multipliers 208 through 212 multiply the signals from multipliers 201 through 205 with direct current voltages $C_{32}$ through $C_{36}$, respectively. Summing means 215 sums signals from multipliers 208, 210 and 212 with a direct current voltage $C_{30}$.

Summing means 216 sums the signals from multipliers 209, 211 and 206. Subtracting means 218 subtracts the signal from summing means 216 from the signal provided by summing means 215 to provide a difference signal $E_A$. Since $P_3$ in most instances is less than 1.0, the signal from amplifier 190 will be negative. To assure that comparator sees that the signal from amplifier 190 and signal $E_A$ will approach equality, an inverter 219 inverts signal $E_A$ to provide signal $E_1$. It should be noted that when $P_3$ will be greater than 1.0, inverter 219 is omitted. As these signals increase in value, signal $E_1$ increases in a negative direction. As noted before, when signal $E_1$ exceeds log $P_3$, flip-flop 193 is triggered to the set state; as a result its $\overline{Q}$ signal goes to a low level thereby disabling AND gate 195 to stop the counting by counter means 198. The change in amplitude of the $\overline{Q}$ signal from flip-flop 193 triggers a one shot multivibrator 220 causing one shot 220 to provide a pulse to latching means 221. Latching means 221 stores the digital signals provided by counter means 198 in response to the pulse from one-shot 220. Latching means 221 provides digital signals to a digital-to-analog converter 225 which provides an analog signal $Z_B$. Computer 55 also includes reset pulse means 227 which periodically provides reset pulses to flip-flop 193 and to counter means 198.

Figure 11:
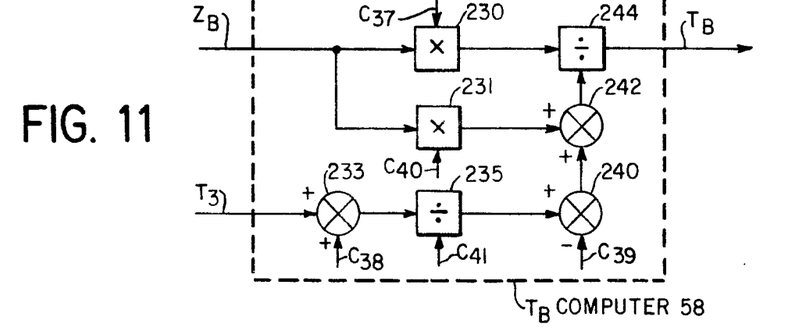

Referring now to FIG. 11, which shows $T_B$ computer 58, signal $Z_B$ is provided to multipliers 230, 231 where it is multiplied with direct current voltages $C_{37}$ and $C_{40}$, respectively. Summing means 233 sums a direct current voltage $C_{38}$ with signal $T_3$ to provide a sum signal to a divider 235. Divider 235 divides a direct current voltage $C_{41}$ with the sum signal to provide a signal to subtracting means 240. Subtracting means 240 subtracts a direct current voltage $C_{39}$ from the signal provided by divider 235 to provide a difference signal. Summing means 242 sums the signals provided by multiplier 231 and subtracting means 240 to provide a sum signal. A divider 244 divides the signal provided by multiplier 230 with the sum signal from summing means 242 provides the signal $T_B$.

$Z_F$ computer 60 is identical in construction and operation as $Z_B$ computer 55 except that a direct current voltage $P_F$ replaces signal $P_3$ in the operation of $Z_F$ computer 60.

Figure 12:
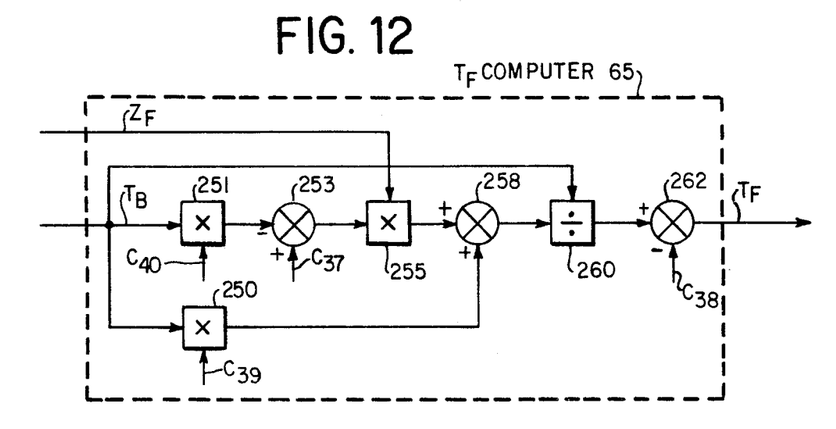

Referring now to FIG. 12, $T_F$ computer 65 includes multipliers 250 and 251 which multiply signal $T_B$ with direct current voltages $C_{39}$ and $C_{40}$, respectively, to provide product signals. Subtracting means 253 subtracts the product signal provided by multiplier 251 from a direct current voltage $C_{37}$ to provide a signal corresponding to the term $(C_{37}-C_{40}T_B)$ in equation 12. A multiplier 255 multiplies the signal provided by subtracting means 253 with signal $Z_F$ to provide a product signal which is summed with the product signal from multiplier 250 by summing means 258. A divider 260 divides signal $T_B$ with a signal provided by summing means 258 to provide another signal to subtracting means 262. Subtracting means 262 subtracts direct current voltage $C_{38}$ from the signal from divider 260 to provide signal $T_F$.

Figure 13:
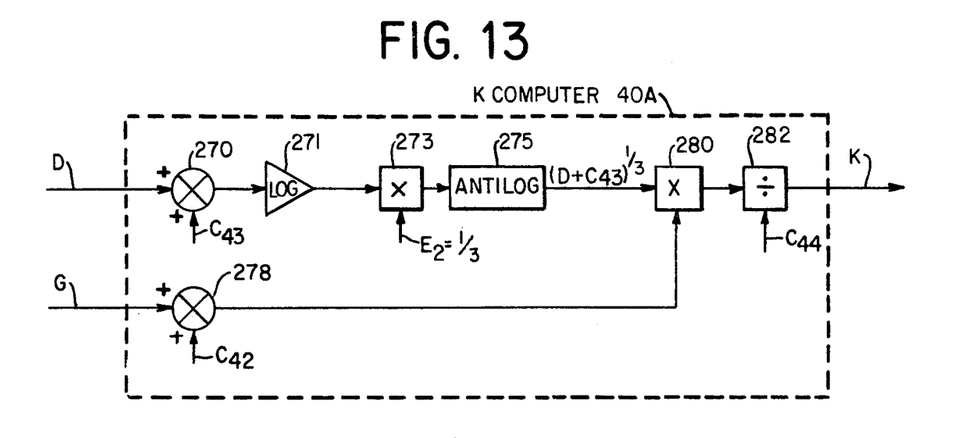
FIG. 13 is a detailed block diagram of an alternate K computer utilized in a second embodiment of the present invention.

As noted before, in another embodiment where a low boiling point stock such as kerosine is being analyzed, viscosity analyzer 31 is replaced with ASTM 50% analyzer (not shown) which provides a signal D corresponding to the ASTM 50% point. The K computer 40 is replaced with a K computer 40A shown in FIG. 13. In computer 40A, summing means 270 sums signal D with a direct current voltage $C_{43}$. A logarithmic amplifier 271 provides a signal log D, corresponding to the logarithm of the sum signal provided by the summing means 270, to a multiplier 273. Multiplier 273 multiplies signal log D with direct current voltage $E_2$, corresponding to a value of $\frac{1}{3}$. An antilog circuit 275, which may be of a conventional type, receives the product signal from multiplier 273 and provides a signal corresponding to $(D+C_{43})^{1/3}$ in equation 2A. Summing means 278 sums signal G with a direct current voltage $C_{42}$ to provide a sum signal. A multiplier 280 multiplies the sum signal from summing means 278 with the signal from antilog circuit 275 to provide a product signal to a divider 282. Divider 282 divides the product signal from multiplier 280 with a direct current voltage $C_{44}$ to provide a signal K. Signal K is then utilized in the same manner with all the other circuitry as the signal K used in the first embodiment.

It would be obvious to one skilled in the art that the arrangement of any or all the computer circuits and operation of circuits on all the signals can be accomplished by a general purpose digital computer specially programmed to accomplish the invention hereinbefore described. It can be appreciated that the present invention as hereinbefore described is not restricted to a hardwired special analog computer.

The present invention as herein described in one embodiment provides a signal corresponding to the flash point of a high boiling point stock such as light lube oil, while in another embodiment, it provides a flash point signal for a low boiling point stock as a kerosine.

What is claimed is:

1. A flash point analyzer for use with a steam stripper having a bottom tray and receiving a stream of material and steam and providing a product, comprising means for sensing the temperatures of the material, the steam and the product and providing signals $T_1$, $T_2$ and $T_3$, respectively, corresponding thereto; means for sensing the flow rates of the steam and the product and providing corresponding signals $F_2$ and $F_3$, respectively, corresponding thereto; means for sensing a pressure in the stripper and providing a signal P representative thereof; means for sampling the product and providing signals corresponding to at least two predetermined parameters of the product; and means connected to all the sensing means and to the sampling means for providing a signal corresponding to the flash point temperature of the product in accordance with the temperature signals $T_1$, $T_2$ and $T_3$, the flow rate signals $F_2$ and $F_3$, the pressure signal P and the parameter signals.

2. A flash point analyzer as described in claim 1 in which one of the parameter signals is a signal G corresponding to the API gravity of the product; and the flash point means includes K signal means connected to the sampling means and providing a signal K corresponding to the Watson K factor in accordance with the other parameter signal and signal G, M signal means connected to the sampling means and to the K signal means for providing a signal M corresponding to the molecular weight of the product in accordance with signals K and G, $T_4$ signal means connected to the temperature sensing means for providing a signal $T_4$, corresponding to the temperature of liquid flowing to the bottom tray in the stripper, in accordance with signals $T_1$ and $T_3$, enthalpy signal means connected to the K signal means, to the $T_4$ signal means, to the sampling means and to the temperature sensing means for providing signals $H_{L3}$, $H_{L4}$ and $H_{V3}$, corresponding to the enthalpy of liquid leaving the bottom tray, the enthalpy of liquid flowing to the bottom tray and the enthalpy of vapor from the bottom tray, respectively, in accordance with signals K, G, $T_3$ and $T_4$, $F_5$ signal means connected to the enthalpy signal means, to the temperature sensing means, to the flow rate sensing means and to the sampling means for providing a signal $F_5$ corresponding to the flow rate of vapor stripped from the bottom tray in accordance with the signals $T_3$, $F_3$, $T_2$, $F_2$, $H_{V3}$, $H_{L3}$, $H_{L4}$, and G; $P_3$ signal means connected to the M signal means, to the flow rate sensing means, to the pressure sensing means and to the $F_5$ signal means for providing a signal $P_3$, corresponding to the partial pressure of hydrocarbon vapors above the bottom tray, in accordance with signals M, $F_5$, $F_2$ and P; $T_B$ signal means connected to the $P_3$ signal means and to the temperature sensing means for providing a signal $T_B$ corresponding to the estimated boiling point of the product in accordance with signals $P_3$ and $T_3$; $Z_F$ signal means for providing a signal $Z_F$ corresponding to a first intermediate variable, and $T_F$ signal means connected to the $T_B$ and to $Z_F$ signal means for providing the signal $T_F$ corresponding to the flash point temperature of the product in accordance with the signal $T_B$ and $Z_F$.

3. A flash point analyzer as described in claim 2 in which the M signal means also receives direct current voltages $C_{22}$, $C_{23}$, $C_{24}$, $C_{25}$ and $C_{26}$ and provides the M signal in accordance with the signals K and G, and direct current voltages $C_{22}$, $C_{23}$, $C_{24}$, $C_{25}$ and $C_{26}$ and with the following equation:

$$M = C_{22}[G - C_{23}(K - C_{24})]^2 - C_{25}[G - C_{23}(K - C_{24})] + C_{26},$$

where $C_{22}$ through $C_{26}$ are constants.

4. A flash point analyzer as described in claim 3 in which the $T_4$ signal means provides signal $T_4$ in accordance with signals $T_1$ and $T_3$, direct current voltage N and the following equation:

$$T_4 = T_3 + (T_1 - T_3)/N,$$

where $N$ is the number of trays in the stripper.

5. A flash point analyzer as described in claim 4 in which the enthalpy signal means includes $H_{L4}$ signal means connected to the $T_4$ signal means, to the sampling means and to the K signal means and receiving direct current voltages $C_4$ through $C_{11}$ for providing signal $H_{L4}$ in accordance with signals $T_4$, G and K, direct current voltages $C_4$ through $C_{11}$ and the following equation:

$$H_{L4} = C_4(C_5K + C_6)[(C_7 + C_8G)T_4 + C_9(C_{10} + C_{11}G)T_4^2],$$

where $C_4$ through $C_{11}$ are constants; $H_{L3}$ signal means connected to the temperature sensing means, to the sampling means and to the K signal means and receiving direct current voltages $C_4$ through $C_{11}$ for providing signal $H_{L3}$ in accordance with signals $T_3$, G and K, direct current voltages $C_4$ through $C_{11}$ and the following equation:

$$H_{L3} = C_4(C_5K + C_6)[(C_7 + C_8G)T_3 + C_9(C_{10} + C_{11}G)T_3^2],$$

where $C_4$ through $C_{11}$ are constants; and $H_{V3}$ signal means connected to the K signal means, to the temperature sensing means, to the sampling means and receiving direct current voltages $C_{12}$ through $C_{18}$ for providing signal $H_{V3}$ in accordance with signals $K$, $T_3$ and $G$, direct current voltages $C_{12}$ through $C_{18}$, and the following equation:

$$H_{V3} = C_{12}T_3^2 + C_{13}T_3 + C_{14} + C_{15}G + C_{16}(K - C_{17})(T_3 - C_{18}),$$

where $C_{12}$ through $C_{18}$ are constants.

6. A flash point analyzer as described in claim 5 in which the $F_5$ signal means also receives direct current voltages $C_{19}$, $C_{20}$ and $C_{21}$ and provides signal $F_5$ in accordance with signals $F_2$, $F_3$, $T_2$, $T_3$, $H_{V3}$, $H_{L3}$ and $H_{L4}$, direct current voltages $C_{19}$, $C_{20}$ and $C_{21}$ and the following equation:

$$F_5 = \{F_3[C_{19}/(C_{20}+G)](H_{L4} - H_{L3}) + C_{21}(T_2 - T_3)F_2\}/(H_{V3} - H_{L4}),$$

where $C_{19}$, $C_{20}$ and $C_{21}$ are constants.

7. A flash point analyzer as described in claim 6 in which the $P_3$ signal means also receives direct current voltages $C_{27}$, $C_{28}$, $C_{29}$ and $\Delta P$ and provides signal $P_3$ in accordance with signals M, $F_5$, $F_2$ and P, direct current voltages $C_{27}$, $C_{28}$ and $C_{29}$ and $\Delta P$, and the following equation:

$$P_3 = (C_{27}(P + \Delta P)(F_5/M)/C_{28}(F_5/M - F_2/C_{29}),$$

where $C_{27}$, $C_{28}$ and $C_{29}$ are constants and $\Delta P$ is a predetermined pressure drop in the stripper.

8. A flash point analyzer as described in claim 7 in which the $T_B$ signal means includes $Z_B$ signal means connected to the $P_3$ signal means and receiving direct current voltages $C_{30}$ through $C_{36}$ for providing a signal $Z_B$ corresponding to a second intermediate variable in accordance with the signal $P_3$, direct current voltages $C_{30}$ through $C_{36}$ and the following equation:

$$\log P_3 = C_{30} - C_{31}Z_B + C_{32}Z_B^2 - C_{33}Z_B^3 + C_{34}Z_B^4 - C_{35}Z_B^5 + C_{36}Z_B^6,$$

where $C_{30}$ through $C_{36}$ are constants, and $T_B$ circuit means connected to the temperature sensing means and to the $Z_B$ signal means and receiving direct voltages $C_{37}$ through $C_{41}$ for providing signal $T_B$, in accordance with signals $Z_B$ and $T_3$, direct current voltages $C_{37}$ through $C_{41}$ and the following equation:

$$T_B = (C_{37})(Z_B)/[C_{41}/(T_3 + C_{38}) - C_{39} + C_{40}Z_B],$$

where $C_{37}$ through $C_{41}$ are constants.

9. A flash point analyzer as described in claim 8 in which the $Z_F$ signal means receives direct current voltages $P_F$ and $C_{30}$ through $C_{36}$ and provides signal $Z_F$ in accordance with the direct current voltages and the following equation:

$$\log P_F = C_{30} - C_{31}Z_F + C_{32}Z_F^2 - C_{33}Z_F^3 + C_{34}Z_F^4 - C_{35}Z_F^5 + C_{36}Z_F^6,$$

where $P_F$ is the vapor pressure at the flash point of the product, and $C_{30}$ through $C_{36}$ are constants.

10. A flash point analyzer as described in claim 9 in which the $T_F$ circuit means also receives direct current voltages $C_{37}$ through $C_{40}$ and provides signal $T_F$ in accordance with signals $T_B$ and $Z_F$, direct current voltages $C_{37}$ through $C_{40}$ and the following equations:

$$T_F = T_B/[Z_F(C_{37} - C_{40}T_B) + C_{39}T_B] - C_{38}.$$

11. A flash point analyzer as described in claim 10 in which the material has high boiling point properties and the sampling means includes means for providing a signal V corresponding to the viscosity of the product as the other parameter signal, and the K signal means receives direct current voltages $C_1$, $C_2$ and $C_3$ and provides signal K in accordance with signals V and G, direct current voltages $C_1$, $C_2$ and $C_3$ and the following equation:

$$K = C_1 + C_2G - C_3/V,$$

where $C_1$, $C_2$ and $C_3$ are constants.

12. A flash point analyzer as described in claim 10 in which the material has low boiling point properties, and the sampling means includes means for providing a signal D corresponding to the ASTM 50% point of the product as the other parameter signal, and the K signal means receives direct current voltages $C_{42}$, $C_{43}$ and $C_{44}$ and provides signal K in accordance with signals D and G, direct current voltages $C_{42}$, $C_{43}$ and $C_{44}$ and the following equation:

$$K = [(G + C_{42})(D + C_{43})^{1/3}]/C_{44},$$

where $C_{42}$, $C_{43}$ and $C_{44}$ are constants.

13. A flash point analyzing method for use with a steam stripper having a bottom tray and receiving a stream of material and steam and providing a product, which comprises the steps of sensing the temperatures of the material, the steam and the product; providing signals $T_1$, $T_2$ and $T_3$ corresponding to the sensed temperatures of the material, the steam and the product, respectively, sensing the flow rates of the steam and the product; providing signals $F_2$ and $F_3$ corresponding to the sensed flow rates of the steam and the product, respectively; sensing a pressure in the stripper; providing a signal P representative of the sensed pressure; sampling the product, providing signals corresponding to at least two predetermined parameters of the product in accordance with the sample; and providing a signal corresponding to the flash point temperature of the product in accordance with the temperature signals $T_1$, $T_2$ and $T_3$, the flow rate signals $F_2$ and $F_3$, the pressure signal P and the parameter signals.

14. A method as described in claim 13 in which one of the parameter signals is a signal G corresponding to the API gravity of the product; and the flash point signal step includes providing a signal K corresponding to the Watson K factor in accordance with the other parameter signal and signal G; providing a signal M corresponding to the molecular weight of the product in accordance with signals K and G; providing a signal $T_4$, corresponding to the temperature of liquid flowing to the bottom tray in the stripper, in accordance with signals $T_1$ and $T_3$; providing signals $H_{L3}$, $H_{L4}$ and $H_{V3}$, corresponding to the enthalpy of liquid leaving the bottom tray, the enthalpy of liquid flowing to the bottom tray and the enthalpy of vapor from the bottom tray, respectively, in accordance with signals K, G, $T_3$ and $T_4$; providing a signal $F_5$ corresponding to the flow rate of vapor stripped from the bottom tray in accordance with signals $T_3$, $F_3$, $T_2$, $H_{V3}$, $F_2$, $H_{L3}$, G and $H_{L4}$; providing a signal $P_3$, corresponding to the partial pressure of hydrocarbon vapors above the bottom tray, in accordance with signals M, $F_5$, $F_2$ and P; providing a signal $T_B$ corresponding to the estimated boiling point of the product in accordance with signals $P_3$ and $T_3$; providing a signal $Z_F$ corresponding to a first intermediate variable, and providing the signal $T_F$ corresponding to the flash point temperature of the product in accordance with the signal $T_B$ and $Z_F$.

15. A method as described in claim 14 in which the M signal step also includes providing direct current voltages $C_{22}$, $C_{23}$, $C_{24}$, $C_{25}$ and $C_{26}$, and providing the M signal in accordance with the signals K and G, direct current voltages $C_{22}$, $C_{23}$, $C_{24}$, $C_{25}$ and $C_{26}$ and the following equation:

$$M = C_{22}[G - C_{23}(K - C_{24})]^2 - C_{25}[G - C_{23}(K - C_{24})] + C_{26},$$

where $C_{22}$ through $C_{26}$ are constants.

16. A method as described in claim 15 in which the $T_4$ signal step includes providing signal $T_4$ in accordance with signals $T_1$ and $T_3$, direct current voltage N and the following equation:

$$T_4 = T_3 + (T_1 - T_3)/N,$$

where N is the number of trays in the stripper.

17. A method as described in claim 16 in which the enthalpy signal step includes providing direct current voltages $C_4$ through $C_{11}$, providing signal $H_{L4}$ in accordance with signals K, G and $T_4$, direct current voltages $C_4$ through $C_{11}$ and the following equation:

$$H_{L4} = C_4(C_5K + C_6)[(C_7 + C_8G)T_4 + C_9(C_{10} - C_{11}G)T_4^2],$$

where $C_4$ through $C_{11}$ are constants; providing direct current voltages $C_4$ through $C_{11}$, providing signal $H_{L3}$ in accordance with signals $T_3$, G and K, direct current voltages $C_4$ through $C_{11}$ and the following equation:

$$H_{L3} = C_4(C_5K + C_6)[(C_7 + C_8G)T_3 + C_9(C_{10} + C_{11}G)T_3^2],$$

where $C_4$ through $C_{11}$ are constants, providing direct current voltages $C_{12}$ through $C_{18}$, and providing signal $H_{V3}$ in accordance with signals $T_3$, G and K, direct current voltages $C_{12}$ through $C_{18}$, and the following equation:

$$H_{V3} = C_{12}T_3^2 + C_{13}T_3 + C_{14} + C_{15}G + C_{16}(K - C_{17})(T_3 - C_{18}),$$

where $C_{12}$ through $C_{18}$ are constants.

18. A method as described in claim 17 in which the $F_5$ signal step also includes providing direct current voltages $C_{19}$, $C_{20}$ and $C_{21}$, providing signal $F_5$ in accordance with signals $F_2$, $F_3$, $T_2$, $T_3$, $H_{V3}$, $H_{L3}$ and $H_{L4}$, direct current voltages $C_{19}$, $C_{20}$ and $C_{21}$ and the following equation:

$$F_5 = [F_3[C_{19}/(C_{20}+G)](H_{L4}-H_{L3})+C_{21}(T_2-T_3)F_2]/(H_{V3}-H_{L4}),$$

where $C_{19}$, $C_{20}$ and $C_{21}$ are constants.

19. A method as described in claim 18 in which the $P_3$ signal step also includes providing direct current voltages $C_{27}$, $C_{28}$, $C_{29}$ and $\Delta P$, and providing signal $P_3$ in accordance with signals M, $F_5$, $F_2$ and P, direct current voltages $C_{27}$, $C_{28}$ and $C_{29}$ and $\Delta P$, and the following equation:

$$P_3 = [(C_{27}(P+\Delta P)(F_5/M)]/C_{28}(F_5/M-F_2/C_{29}),$$

where $C_{27}$, $C_{28}$ and $C_{29}$ are constants and $\Delta P$ is a predetermined pressure drop in the stripper.

20. A method as described in claim 19 in which the $T_B$ signal step includes providing direct current voltages $C_{30}$ through $C_{40}$, providing a signal $Z_B$, corresponding to a second intermediate variable, in accordance with the signal $P_3$, direct current voltages $C_{30}$ through $C_{36}$ and the following equation:

$$\log P_3 = C_{30}-C_{31}Z_B+C_{32}Z_B^2-C_{33}Z_B^3+C_{34}Z_B^4-C_{35}Z_B^5+C_{36}Z_B^6$$

where $C_{30}$ through $C_{36}$ are constants, providing a signal $T_B$ in accordance with signals $T_3$ and $Z_B$, voltages $C_{37}$ through $C_{40}$ and the following equation:

$$T_B = (C_{37})(Z_B)/[C_{41}/(T_3+C_{38})-C_{39}+C_{40}Z_B],$$

where $C_{37}$ through $C_{40}$ are constants.

21. A method as described in claim 20 in which the $Z_F$ signal step includes providing a direct current voltage $P_F$, and providing signal $Z_F$ in accordance with voltages $P_F$ and $C_{30}$ through $C_{36}$ and the following equation:

$$\log P_F = C_{30}-C_{31}Z_F+C_{32}Z_F^2-C_{33}Z_F^3+C_{34}Z_F^4-C_{35}Z_F^5+C_{36}Z_F^6$$

where $P_F$ is the vapor pressure at the flash point of the product and $C_{30}$ through $C_{36}$ are constants.

22. A method as described in claim 21 in which the $T_F$ signal step includes providing direct current voltages $C_{37}$ through $C_{40}$, and providing signal $T_F$ in accordance with signals $T_B$ and $Z_F$, direct current voltages $C_{37}$ through $C_{40}$ and the following equation:

$$T_F = T_B/[Z_F(C_{37}-C_{40}T_B)+C_{39}T_B]-C_{38}.$$

23. A method as described in claim 22 in which the material has high boiling point properties and the parameter signal step includes providing a signal V corresponding to the viscosity of the product as the other parameter signal, and the K signal step includes providing direct current voltages $C_1$, $C_2$ and $C_3$, and providing signal K in accordance with signals V and G, direct current voltages $C_1$, $C_2$ and $C_3$ and the following equation:

$$K = C_1+C_2G-C_3/V,$$

where $C_1$, $C_2$ and $C_3$ are constants.

24. A method as described in claim 23 in which the material has low boiling point properties, and the parameter signal step includes providing a signal D corresponding to the ASTM 50% point of the product as the other parameter signal, and the K signal step includes providing direct current voltages $C_{42}$, $C_{43}$ and $C_{44}$, and providing signal K in accordance with signals D and G, direct current voltages $C_{42}$, $C_{43}$ and $C_{44}$ and the following equation:

$$K = [(G+C_{42})(D+C_{43})^{1/3}]/C_{44},$$

where $C_{42}$, $C_{43}$ and $C_{44}$ are constants.

* * * * *